United States Patent
Shin et al.

(10) Patent No.: US 10,595,833 B2
(45) Date of Patent: Mar. 24, 2020

(54) SURGICAL DEVICE

(71) Applicant: STARMED CO., LTD., Gyeonggi-do (KR)

(72) Inventors: Kyung Hoon Shin, Gyeonggi-do (KR); Dong Un Kim, Gyeonggi-do (KR); Hyuk Lim, Gyeonggi-do (KR)

(73) Assignee: STARMED CO., LTD., Gyeonggi-si (KR)

( * ) Notice: Subject to any disclaimer, the term of this patent is extended or adjusted under 35 U.S.C. 154(b) by 0 days.

(21) Appl. No.: 15/551,959

(22) PCT Filed: Jun. 20, 2016

(86) PCT No.: PCT/KR2016/006499
§ 371 (c)(1),
(2) Date: Aug. 18, 2017

(87) PCT Pub. No.: WO2016/204584
PCT Pub. Date: Dec. 22, 2016

(65) Prior Publication Data
US 2018/0103940 A1 Apr. 19, 2018

(30) Foreign Application Priority Data

Jun. 19, 2015 (KR) .......................... 10-2015-0087131

(51) Int. Cl.
*A61B 10/04* (2006.01)
*A61B 10/02* (2006.01)
(Continued)

(52) U.S. Cl.
CPC .............. *A61B 10/04* (2013.01); *A61B 1/018* (2013.01); *A61B 10/02* (2013.01);
(Continued)

(58) Field of Classification Search
CPC ..... A61B 10/04; A61B 10/02; A61B 10/0233; A61B 18/1445; A61B 18/14; A61M 5/20;
(Continued)

(56) References Cited

U.S. PATENT DOCUMENTS 5,254,106 A * 10/1993 Feaster ............... A61F 9/00736
604/272
5,366,490 A * 11/1994 Edwards .................. A61N 1/40
607/99

(Continued)

FOREIGN PATENT DOCUMENTS

JP     2000-107299 A    4/2000
JP     2000-287992 A   10/2000
(Continued)

OTHER PUBLICATIONS

International Search Report for Application No. PCT/KR2016/006499 dated Oct. 14, 2016.

*Primary Examiner* — Laura A Bouchelle
*Assistant Examiner* — Mark A Igel
(74) *Attorney, Agent, or Firm* — Novick, Kim & Lee, PLLC; Jae Youn Kim

(57) ABSTRACT

The present invention relates to a surgical device. The surgical device may include: a needle device; an aspiration device, which is attached to or detached from the needle device, for tissue sampling; an injection device, which is attached to or detached from the needle device, for drug injection; and an electrode device, which is attached to or detached from the needle device, for thermal treatment. Therefore, any one of the aspiration device, the injection device, and the electrode device is attached to or detached from the needle device, thereby being capable of performing tissue sampling, drug injection, and thermal treatment. Thus, the time and costs required for tissue sampling, drug injec- (Continued)

tion, and thermal treatment are reduced and foreign substances can be prevented from flowing into a surgical site in advance.

11 Claims, 13 Drawing Sheets

(51) Int. Cl.
*A61B 18/14* (2006.01)
*A61B 1/018* (2006.01)
*A61J 15/00* (2006.01)
*A61M 5/20* (2006.01)
*A61M 5/31* (2006.01)
*A61M 5/32* (2006.01)
*A61M 5/315* (2006.01)

(52) U.S. Cl.
CPC .......... *A61B 10/0283* (2013.01); *A61B 18/14* (2013.01); *A61B 18/1445* (2013.01); *A61J 15/00* (2013.01); *A61M 5/20* (2013.01); *A61M 5/3148* (2013.01); *A61M 5/3286* (2013.01); *A61B 10/0233* (2013.01); *A61B 2010/045* (2013.01); *A61M 5/315* (2013.01); *A61M 5/3287* (2013.01)

(58) Field of Classification Search
CPC .. A61M 5/3148; A61M 5/3286; A61M 5/315; A61M 5/3287; Y10T 403/59–599; Y10T 403/60; Y10T 74/19447; F16B 21/12
See application file for complete search history.

(56) References Cited

U.S. PATENT DOCUMENTS

| | | | | |
|---|---|---|---|---|
| 5,458,597 A | * | 10/1995 | Edwards | A61B 18/1477 604/21 |
| 5,470,308 A | * | 11/1995 | Edwards | A61B 10/0233 604/22 |
| 5,995,875 A | * | 11/1999 | Blewett | A61B 18/1477 606/41 |
| 6,875,182 B2 | * | 4/2005 | Wardle | A61B 10/0233 600/564 |
| 2002/0026188 A1 | | 2/2002 | Balbierz et al. | |
| 2002/0133148 A1 | * | 9/2002 | Daniel | A61B 18/1477 606/34 |
| 2003/0195433 A1 | * | 10/2003 | Turovskiy | A61B 90/39 600/564 |
| 2005/0267552 A1 | * | 12/2005 | Conquergood | A61B 18/1477 607/96 |
| 2006/0116605 A1 | | 6/2006 | Nakao | |
| 2012/0289901 A1 | * | 11/2012 | Fink | A61B 10/0283 604/117 |
| 2014/0005478 A1 | * | 1/2014 | Kennedy, II | A61B 1/012 600/114 |

FOREIGN PATENT DOCUMENTS

| | | | |
|---|---|---|---|
| JP | 2002065692 A | * | 3/2002 |
| JP | 2002065692 A | | 3/2002 |
| JP | 2009056303 A | | 3/2009 |
| KR | 10-2012-0126707 A | | 11/2012 |
| KR | 10-1286752 B2 | | 7/2013 |
| KR | 10-1596716 B1 | | 2/2016 |

* cited by examiner

[FIG. 1]
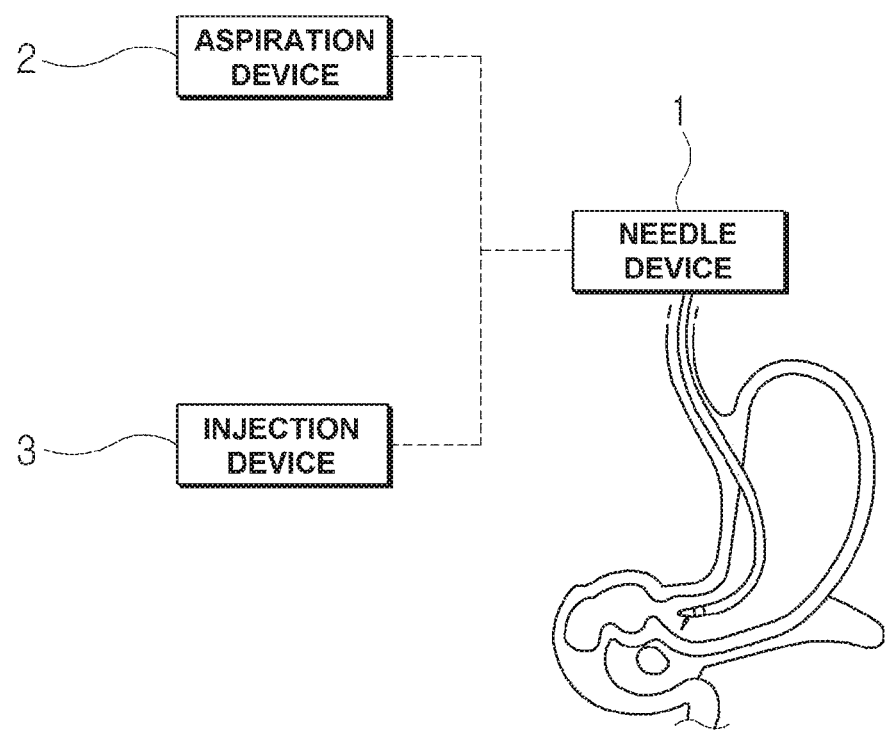

[FIG. 2]
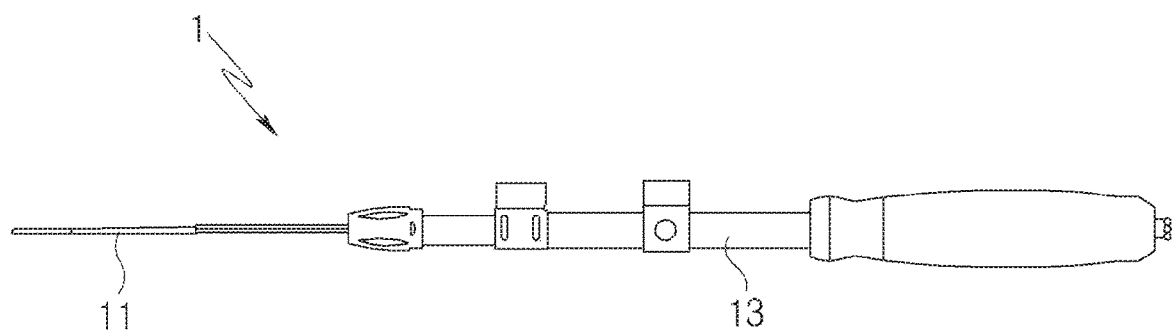

[FIG. 3]
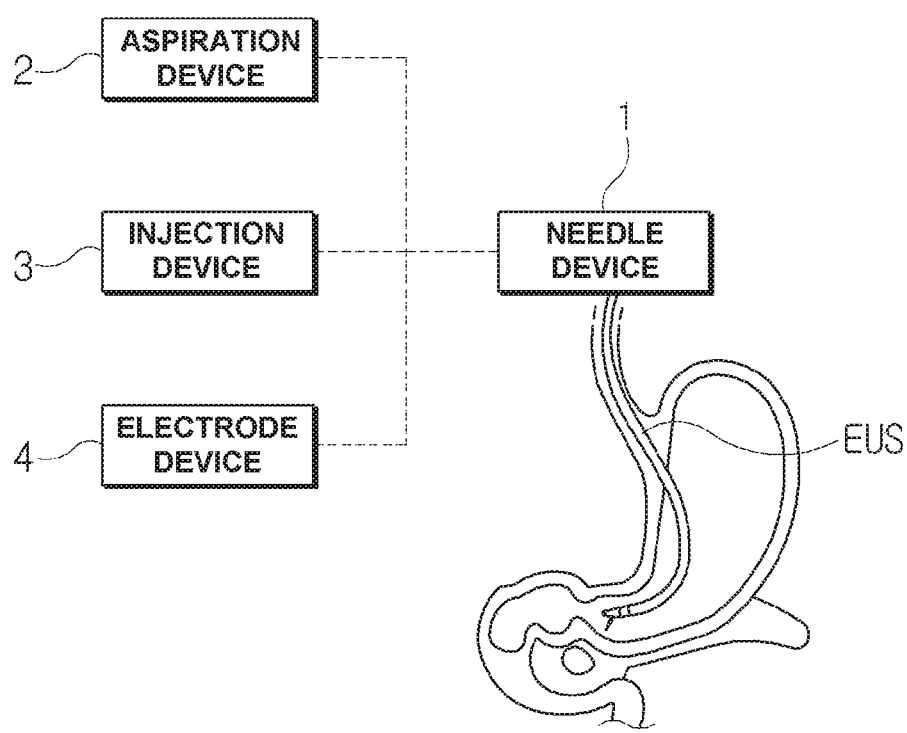

[FIG. 4]
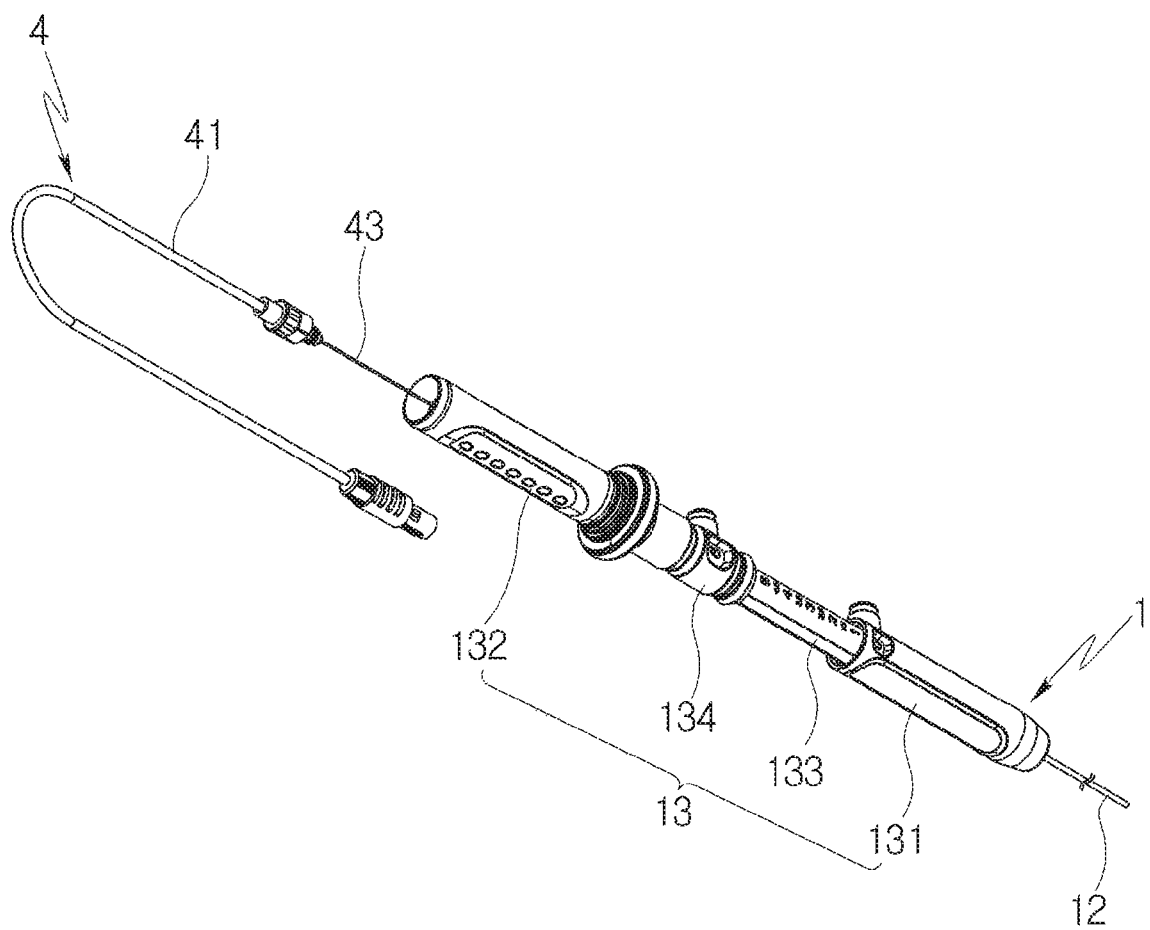

[FIG. 5]
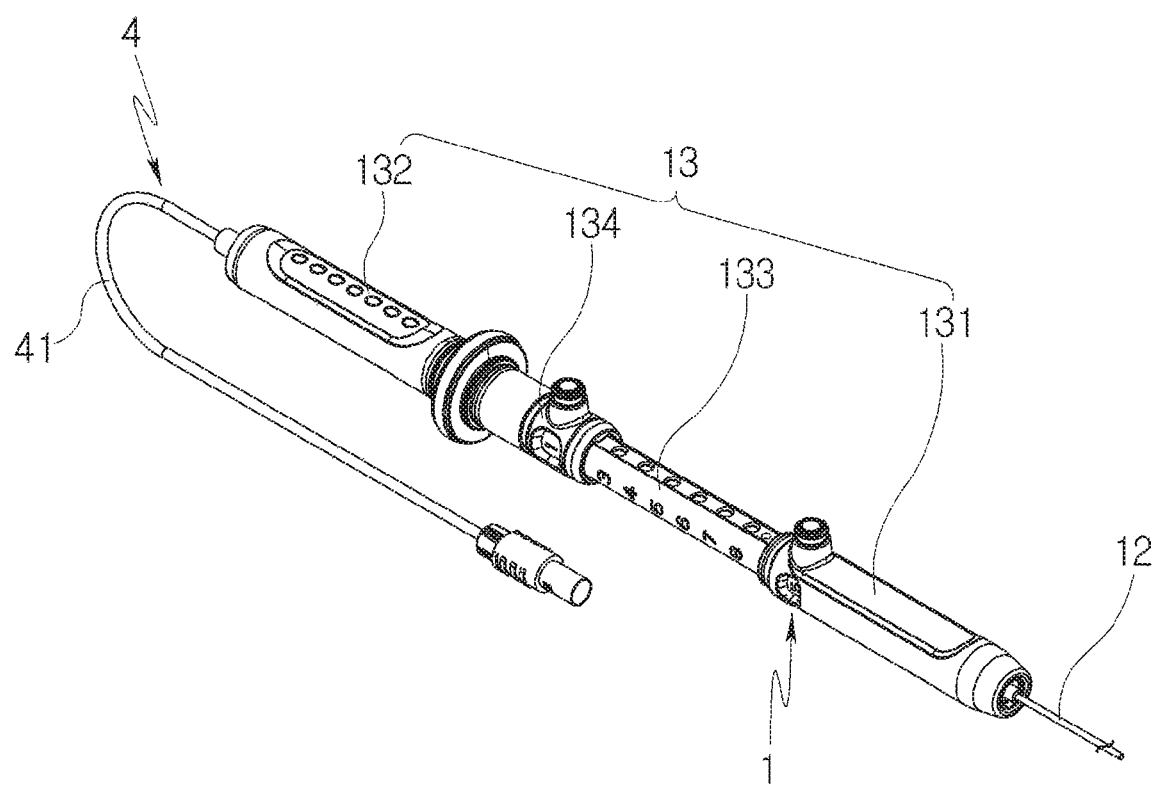

[FIG. 6]
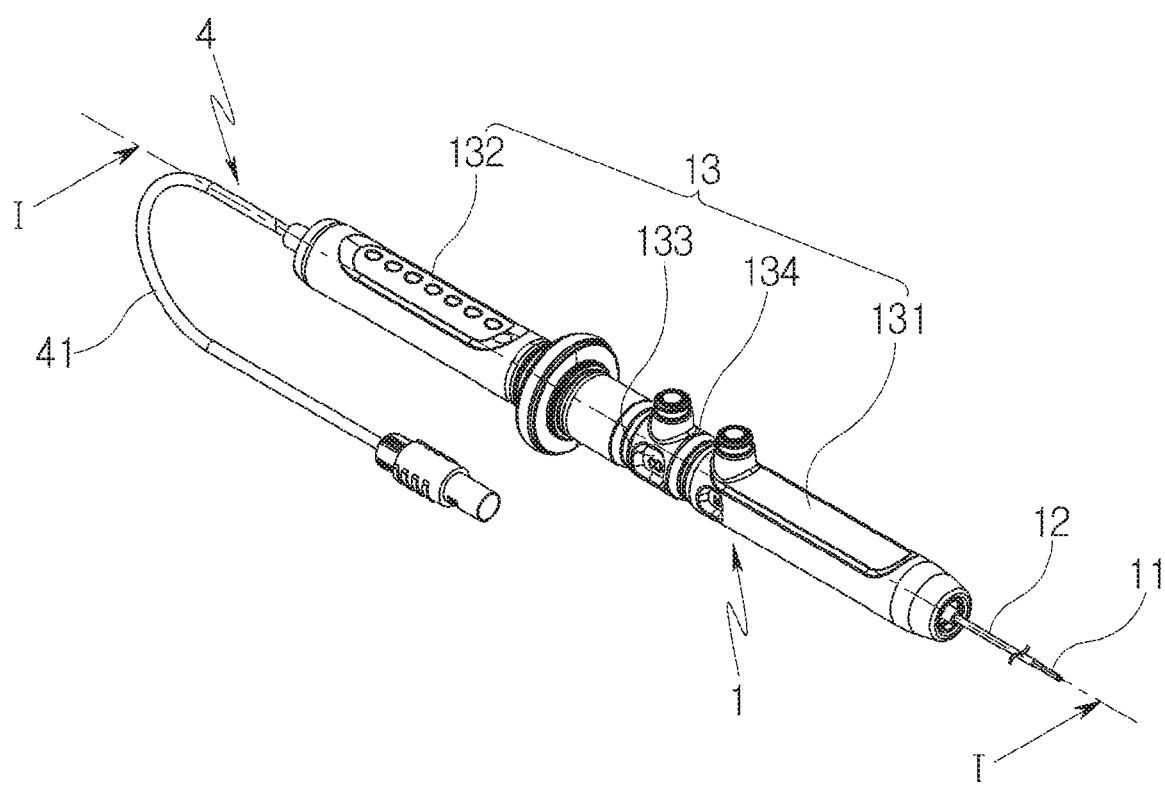

[FIG. 7]
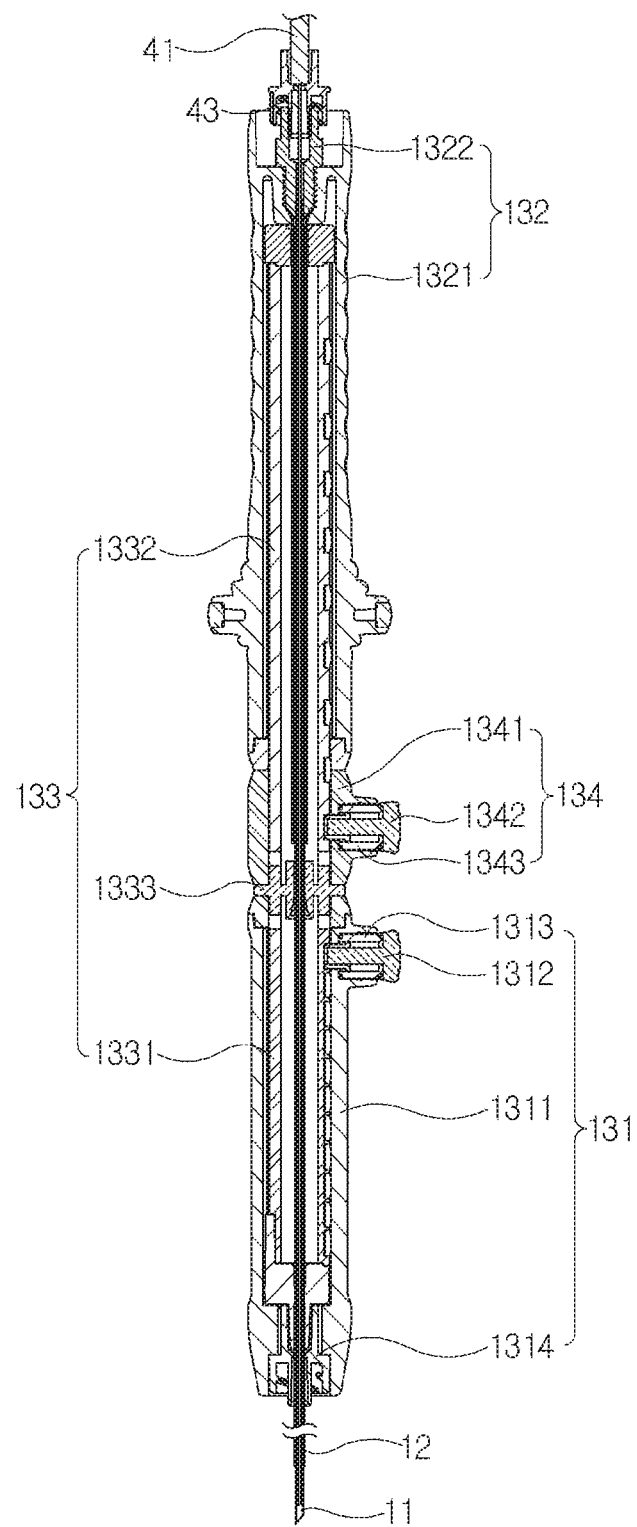

[FIG. 8]
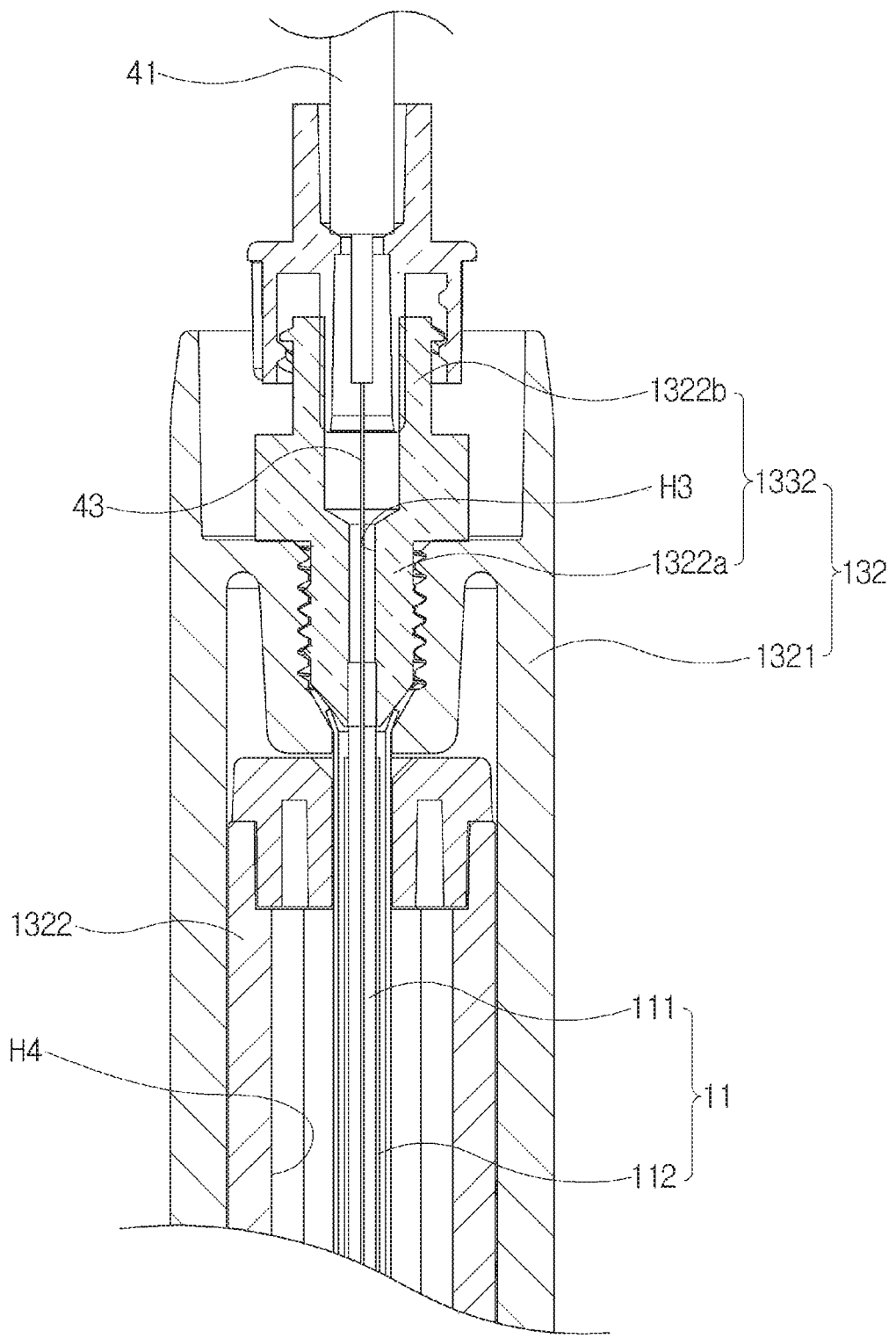

[FIG. 9]
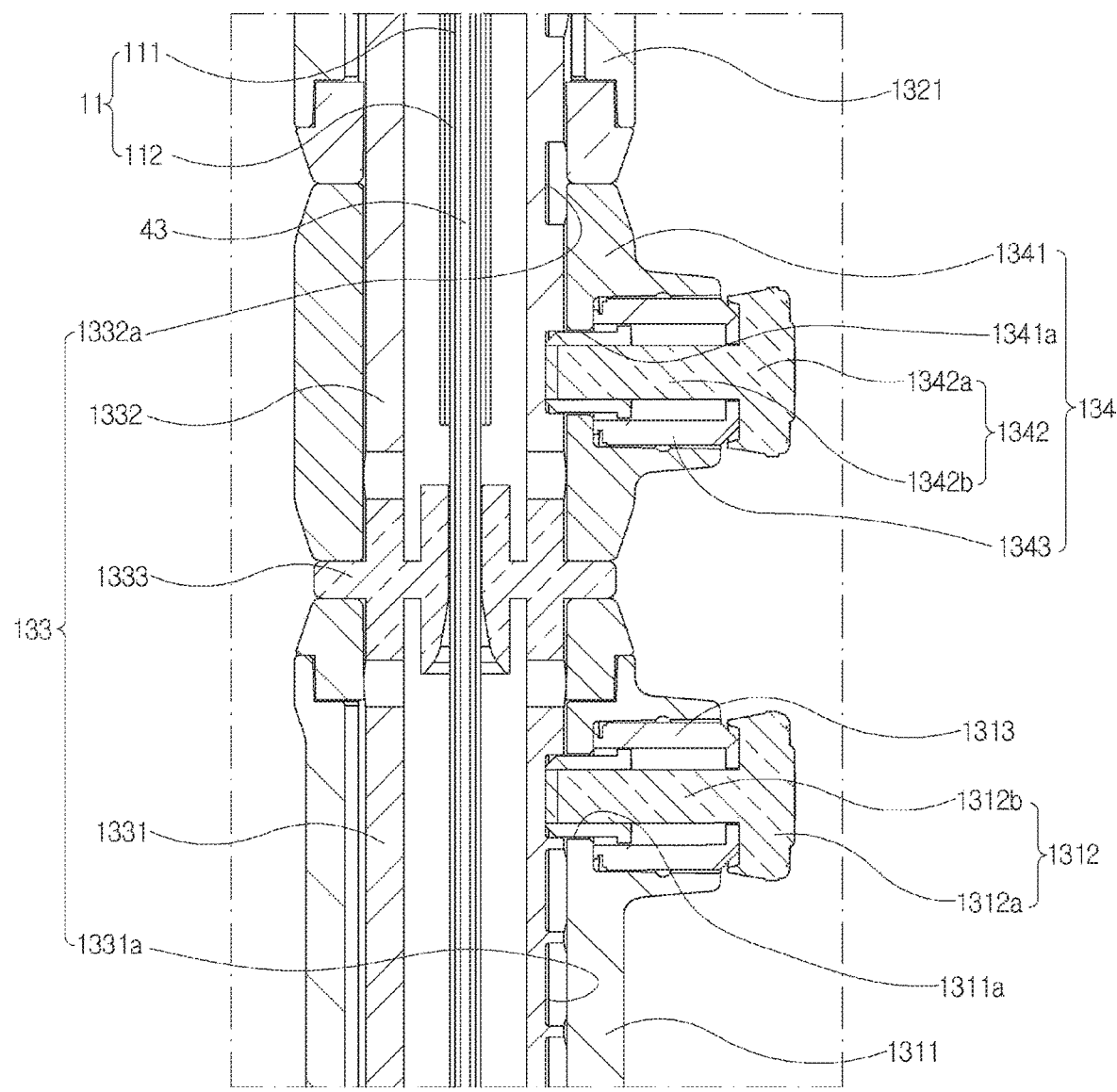

[FIG. 10]
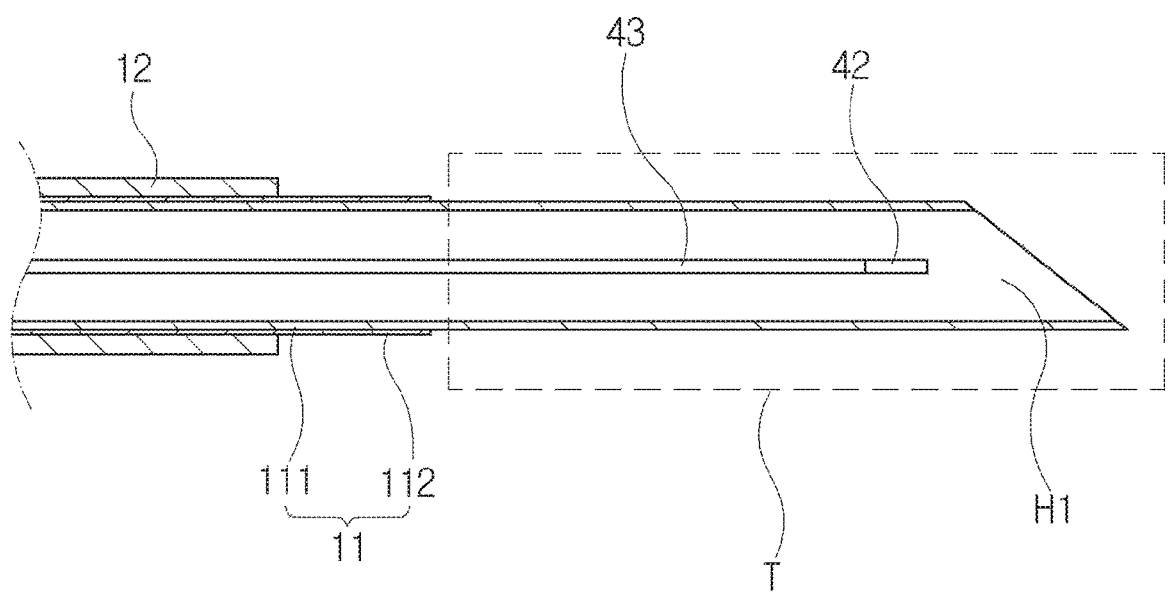

[FIG. 11]
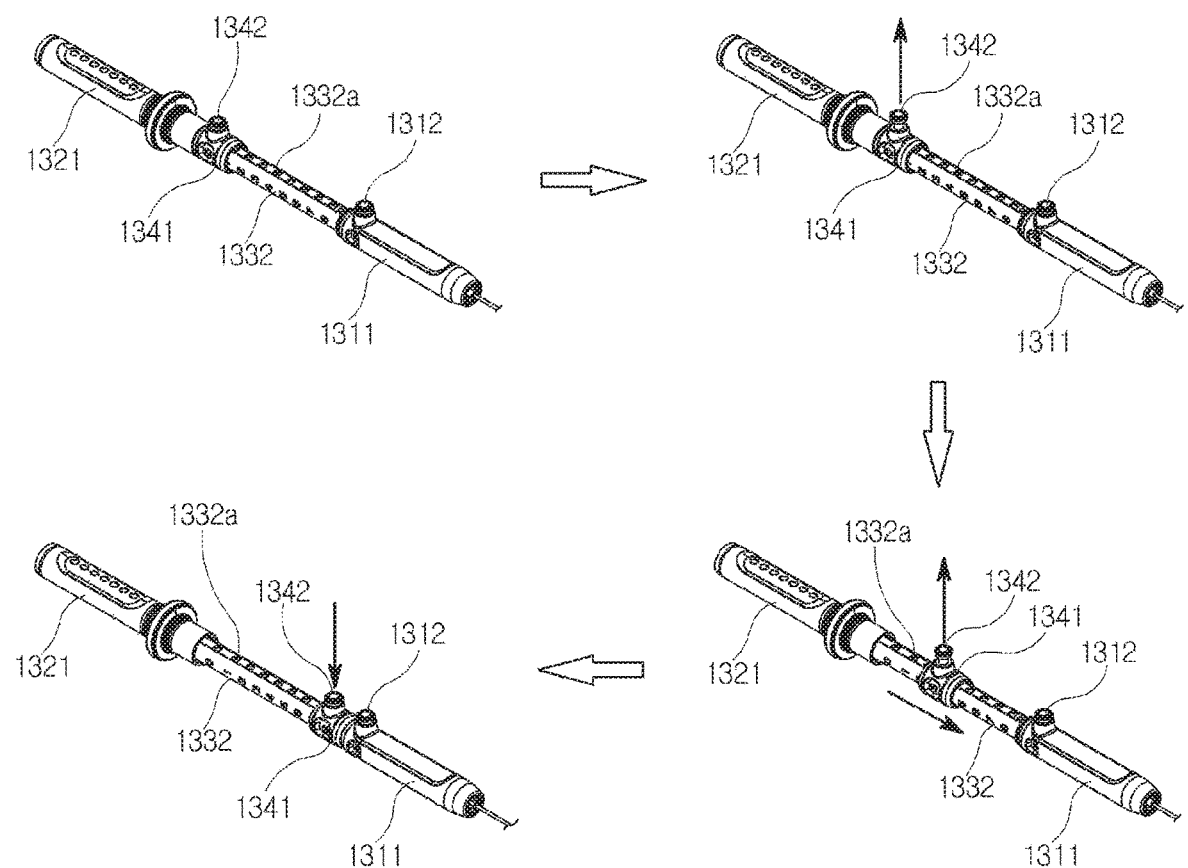

[FIG. 12]
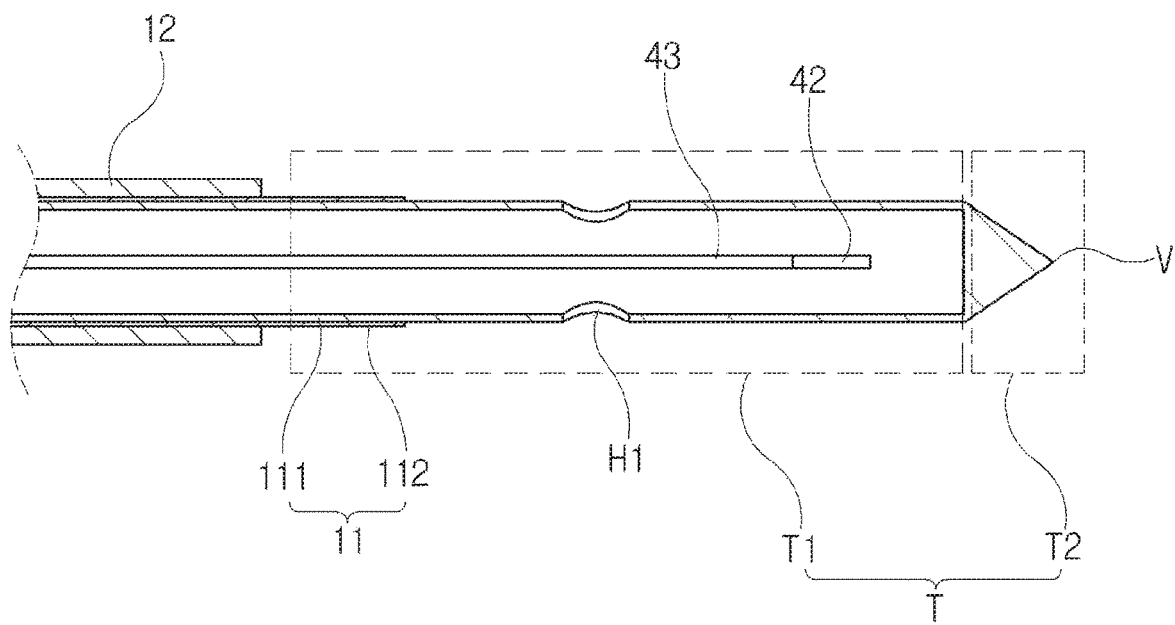

[FIG. 13]
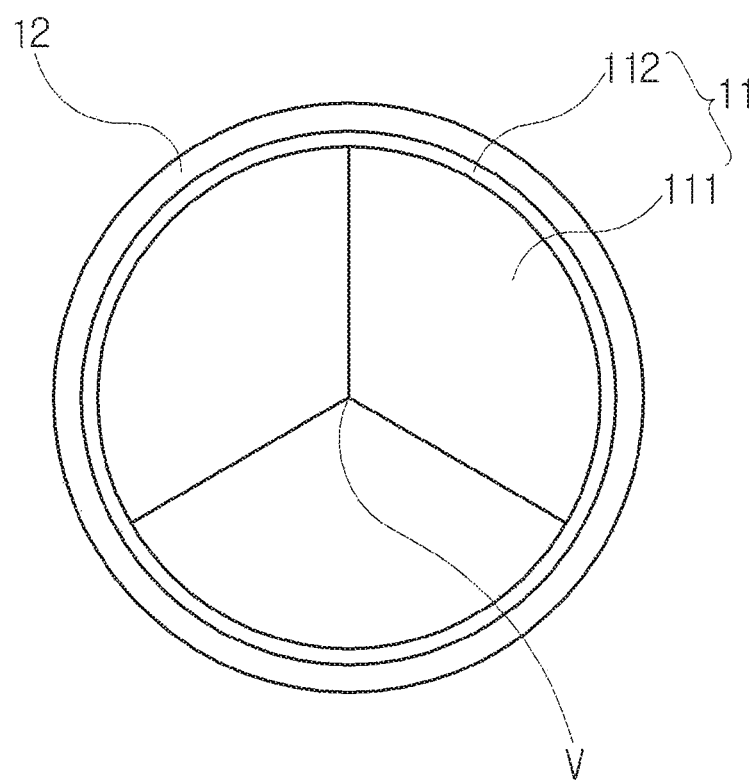

… …

SURGICAL DEVICE

TECHNICAL FIELD

The present invention relates to a surgical device, and more particularly, to a surgical device capable of performing medical treatment through an injection needle.

BACKGROUND ART

In general, a medical endoscope (hereinafter, referred to as an endoscope) is a medical instrument inserted into a body to be able to see the interior of the body.

Recently, a surgical device which is inserted into an endoscope and may perform treatments such as tissue sampling and drug injection while the endoscope is inserted into the body has been disclosed.

FIG. 1 is a system diagram showing the existing surgical device, and FIG. 2 is a front view showing a needle device in the surgical device of FIG. 1.

Referring to FIGS. 1 and 2, the existing surgical device includes a needle device 1, an aspiration device 2, which is attached to or detached from the needle device 1 for tissue sampling, and an injection device 3, which is attached to or detached from the needle device 1, for drug injection.

The needle device 1 includes an injection needle 11 penetrating through the inside of the endoscope and an operating device 13 for moving the injection needle 11.

The aspiration device (not shown) and the injection device (not shown) are provided by a piston type syringe, for example.

In the surgical device having the above configuration, the injection needle 11 is inserted into the endoscope while the endoscope is inserted into the body. Further, the injection needle 11 move forward by the operating device 13 so that a needlepoint of the injection needle 11 protrudes from an end of the endoscope to prick a surgical site. Further, the aspiration device 2 is mounted on the injection needle 11 to perform the tissue sampling or the injection device 3 is mounted on the injection needle 11 to perform the drug injection. After the tissue sampling or the drug injection is completed, the injection needle 11 moves backward and the injection needle 11 is drawn out from the endoscope, by the operating device 13.

The surgical device having the above configuration generally refers to fine needle aspiration (FNA), a fine-needle aspiration device 2, a biopsy device using a fine needle or the like.

However, in such a conventional surgical device, there has been a problem that only the tissue sampling or the drug injection can be made. That is, there has been a problem in that a separate surgical device is provided for additional treatment (for example, thermal treatment), and the surgical device used for the tissue sampling or the drug injection is detached from the endoscope and then the separate surgical device is inserted into the endoscope. Therefore, there has been a problem that the separate surgical device is provided, and the time and costs required to replace the separate surgical device with the surgical device used for the tissue sampling or the drug injection are increased. In addition, there has been a problem in that when the surgical device is replaced, the surgical device for additional treatment is injected into sites other than an original surgical site. In addition, there has been a problem in that foreign substances flow into the surgical site during the process of replacing the surgical device.

DISCLOSURE

Technical Problem

An object of the present invention is to provide a surgical device capable of performing tissue sampling, drug injection, and thermal treatment.

Technical Solution

In accordance with one aspect of the present invention, a surgical device, includes: a needle device; an aspiration device, which is attached to or detached from the needle device, for tissue sampling; an injection device, which is attached to or detached from the needle device, for drug injection; and an electrode device, which is attached to or detached from the needle device, for thermal treatment.

The electrode device may be formed as an RF electrode device.

An injection needle of the needle device may include: a first site formed as a hollow tube and having an injection hole provided at a needlepoint; and a second site surrounding at least a part of the first site, and the first site may be made of a conductive material and the second site may be made of an insulating material.

A needlepoint of the first site may not be surrounded by the second site.

The electrode device may include: a power cable electrically connected to the first site of the injection needle; and a control device applying power to the power cable.

The electrode device may include: a temperature sensor inserted into a hollow of the injection needle; and a sensing cable connecting between the temperature sensor and the control device.

The temperature sensor may be positioned at the needlepoint.

The control device may control power applied to the power cable depending on temperature measured by the temperature sensor so that a temperature of the injection needle is maintained to be in a predetermined range.

The control device may apply power to the power cable if the temperature measured by the temperature sensor is smaller than a predetermined value and may not apply power to the power cable if the temperature measured by the temperature sensor is equal to or larger than the predetermined value.

The needlepoint may include: a cylindrical portion having a hollow cylindrical shape; and a vertex portion having a polygonal pyramid or cone shape from a front end surface of the cylindrical portion.

The vertex portion may be formed so that a vertex of the vertex portion is positioned on a central axis of the injection needle.

The injection hole may be formed as the cylindrical portion.

The injection hole may be formed to penetrate in a radial direction of the cylindrical portion.

The injection hole may be formed in plural, and the plurality of injection holes may be arranged at equal intervals along a circumferential direction of the cylindrical portion.

The needle device may include an injection needle and an operating device moving the injection needle, the operating device may include a first grip portion being a movement reference of the injection needle, a second grip portion coupled to the injection needle and approaching and spaced apart from the first grip portion, a guide portion guiding the movement of the second grip portion, and a pawl portion preventing a distance between the first grip portion and the second grip portion from being smaller than a predetermined value, the guide portion may extend in one direction and may be movably inserted into the second grip portion by penetrating through the pawl portion and provided with a plurality of fixing grooves along an extending direction of the guide portion on the outer circumferential surface of the guide portion, and the pawl portion may include a ring through which the guide portion penetrates, a pin movably inserted into the ring and inserted into any one of the plurality of fixing grooves, and an elastic body applying an elastic force to the pin in a direction in which the pin is inserted into the fixing groove.

Advantageous Effects

According to the surgical device of the present invention, any one of the aspiration device, the injection device, and the electrode device is attached to or detached from the needle device, thereby being capable of performing the tissue sampling, the drug injection, and the thermal treatment. Thus, the time and costs required for the tissue sampling, the drug injection, and the thermal treatment can be reduced and foreign substances can be prevented from flowing into the surgical site in advance.

DESCRIPTION OF DRAWINGS

FIG. 1 is a system diagram showing the existing surgical device.

FIG. 2 is a front view showing a needle device in the surgical device of FIG. 1.

FIG. 3 is a system diagram showing a surgical device according to an embodiment of the present invention.

FIG. 4 is an exploded perspective view showing a needle device and an electrode device in the surgical device of FIG. 3.

FIG. 5 is a perspective view showing an appearance in which the needle device and the electrode device of FIG. 4 are coupled with each other.

FIG. 6 is a perspective view showing an appearance in which a needlepoint protrudes in FIG. 5.

FIG. 7 is a cross-sectional view taken along the line I-I of FIG. 6.

FIG. 8 is an enlarged view of a second grip portion of FIG. 7.

FIG. 9 is an enlarged view of a pawl portion of FIG. 7.

FIG. 10 is an enlarged cross-sectional view of the needlepoint of FIG. 7.

FIG. 11 is a perspective view for explaining a principle of adjusting a protruding length of the needlepoint in the needle device of FIG. 6.

FIG. 12 is a cross-sectional view showing another embodiment of the needlepoint in the needle device of FIG. 6.

FIG. 13 is a side view of FIG. 12.

MODE FOR INVENTION

Hereinafter, a surgical device according to embodiments of the present invention will be described in detail with reference to the accompanying drawings.

FIG. 3 is a system diagram showing a surgical device according to an embodiment of the present invention, FIG. 4 is an exploded perspective view showing a needle device and an electrode device in the surgical device of FIG. 3, FIG. 5 is a perspective view showing an appearance in which the needle device and the electrode device of FIG. 4 are coupled with each other, FIG. 6 is a perspective view showing an appearance in which a needlepoint protrudes in FIG. 5, FIG. 7 is a cross-sectional view taken along the line I-I of FIG. 6, FIG. 8 is an enlarged view of a second grip portion of FIG. 7, FIG. 9 is an enlarged view of a pawl portion of FIG. 7, FIG. 10 is an enlarged cross-sectional view of the needlepoint of FIG. 7, and FIG. 11 is a perspective view for explaining a principle of adjusting a protruding length of the needlepoint in the needle device of FIG. 6.

Referring to FIGS. 3 to 11, a surgical device according to an embodiment of the present invention may include a needle device 1; an aspiration device 2, which is attached to or detached from the needle device 1 for tissue sampling; an injection device 3, which is attached to or detached from the needle device 1 for drug injection; and an electrode device 4, which is attached to or detached from the needle device 1 for thermal treatment.

The needle device 1 may include an injection needle 11 to be injected into a surgical site, a tube 12 surrounding the injection needle 11 to protect the injection needle 11, and an operating device 13 for moving the injection needle 11 so that a needlepoint T protrudes from the tube 12 or is inserted into the tube 12.

The injection needle 11 may include a first site 111 formed as a hollow tube and a second site 112 surrounding an outer circumferential surface of the first site 111.

The first site 111 may be made of a conductive material so that power (current) is applied from the electrode device 4 and may be electrically connected to the electrode device 4.

The second site 112 is made of an insulating material so that thermal treatment is made only at the needlepoint T of the first site 111 but does not damage an unintended site, and the needlepoint T of the first site 111 may be formed not to be covered with the second site 112.

The needlepoint T of the first site 111 may be obliquely cut so that a part of a circumference of the needlepoint T stands on end.

Further, the cut surface of the first site 111 may be provided with an injection hole H1 for communicating the hollow of the first site 111 and an outside of the first site 111 with each other.

The tube 12 may be formed as a hollow tube in which an inner diameter of the tube 12 is equal to or larger than an outer diameter of the injection needle 11 (more precisely, second site 112).

One end of the tube 12 is coupled to a first grip portion 131 to be described later, and thus the tube 12 can be fixed to the first grip portion 131 even if the injection needle 11 moves.

The operating device 13 may include the first grip portion 131 being a movement reference of the injection needle 11, a second grip portion 132 coupled to the injection needle 11 and approaching and spaced apart from the first grip portion 131, a guide portion 133 guiding the movement of the first grip portion 131 and the second grip portion 132, and a pawl portion 134 limiting an approach distance between the first grip portion 131 and the second grip portion 132.

The first grip portion 131 may include a first handle 1311 movable with respect to the guide portion 133, a first pin 1312 fixing the first handle 1311 to the guide portion 133, a first elastic body 1313 having one side supported by the first handle 1311 and the other side supported by the first fin 1312, and a tube support portion 1314 fixing the tube 12 to the first handle 1311.

The first handle 1311 may be formed as a hollow tube having a first guide portion 1331 to be described later inserted thereinto and extending in one direction so that the injection needle 11 may penetrate therethrough.

A sidewall of the first handle 1311 may be provided with a first pinhole 1311a through which the first pin 1312 penetrates.

A first pinhole 1311a may be formed to penetrate in a radial direction of the first handle 1311.

The first pin 1312 may include a first head portion 1312a that has a larger diameter than the first pinhole 1311a and a first protrusion 1312b that protrudes from the first head portion 1312a.

The first pin 1312 may be movably coupled to the first handle 1311 in the radial direction of the first handle 1311 by inserting the first protrusion 1312b into the first pinhole 1311a.

The first pin 1312 moves toward a center of the first handle 1311 so that the first protrusion 1312b is inserted into any one of a plurality of first fixing grooves 1331a to be described later, thereby fixing the first handle 1311 to the guide portion 133.

The first pin 1312 may move toward a radial outside of the first handle 1311 so that the first protrusion 1312b is drawn from a first fixing groove 1331a, into which the first protrusion 1312b is inserted, among a plurality of first fixing grooves 1331a to be described later, thereby releasing the fixing of the first handle 1311 to the guide portion 133.

The first elastic body 1313 may be a spring that applies an elastic force to the first pin 1312 in a direction in which the first protrusion 1312b of the first pin 1312 is inserted into a first fixing groove 1331a to be described later.

The tube support portion 1314 may be fastened to one end of the first handle 1311, have the injection needle 11 penetrating therethrough, and fix one end of the tube 12.

The second grip portion 132 may include a second handle 1321 movable with respect to the guide portion 133 and an injection needle support portion 1322 fixing the injection needle 11 to the second handle 1321.

The second handle 1321 may be formed as a hollow tube that has a second guide portion 1332 to be described later inserted thereinto and extends in one direction so that the injection needle 11 can penetrate therethrough.

The injection needle support portion 1322 may cover one end of the second handle 1321, support the injection needle 11, and connect the injection needle 11 to any one of the aspiration device 2, the injection device 3, and the electrode device 4.

More specifically, the injection needle support portion 1322 may be formed as a long hollow tube in one direction.

The injection needle support portion 1322 may include a first coupling portion 1322a formed at one end of the injection needle support portion 1322 and detachably coupled to one end of the second handle 1321, a second coupling portion 1322b formed at the other end of the injection needle support portion 1322 and detachably coupled to any one of the aspiration device 2, the injection device 3, and the electrode device 4, and a communication hole H3 penetrating through the inside of the injection needle support portion 1322 from the first coupling portion 1322a to the second coupling portion 1322b.

The injection needle 11 (more precisely, first site 111) may be inserted into the communication hole H3 to be press-fitted therein.

The communication hole H3 may communicate with a hollow of the injection needle 11 (more precisely, first site 111).

Meanwhile, the injection needle support portion 1322 may be made of a conductive material so that power (current) input from the electrode device 4 may be output to the first site 111 of the injection needle 11.

The guide portion 133 may include a first guide portion 1331 guiding the movement of the first grip portion 131, a second guide portion 1332 guiding the movement of the second grip portion 132, and a stepped portion 1333 interposed between the first guide portion 1331 and the second guide portion 1332.

The first guide portion 1331 may extend in one direction from the stepped portion 1333, may be inserted into the hollow of the first handle 1311 through the other end of the first handle 1311 and may reciprocally move with respect to the first handle 1311.

An outer circumferential surface of the first guide portion 1331 may be provided a first fixing groove 1331a into which the first pin 1312 (more precisely, first protrusion 1312b) is inserted.

The first fixing grooves 1331a may be formed in plural. The plurality of first fixing grooves 1331a may be arranged at equal intervals along the extending direction of the first guide portion 1331.

The second guide portion 1332 may extend in an opposite direction to the extending direction of the first guide portion 1331 from the stepped portion 1333, may be inserted into the hollow of the second handle 1321 through the other end of the second handle 1321, and may reciprocally move with respect to the second handle 1321.

An outer circumferential surface of the second guide portion 1332 may be provided with a second fixing groove 1332a into which a second pin 1342 to be described later is inserted.

The second fixing groove 1332a may be formed in plural. The plurality of second fixing grooves 1332a may be arranged at equal intervals along the extending direction of the second guide portion 1332.

A distance between the second fixing grooves 1332a may be larger than that between the first fixing grooves 1331a.

An outer diameter of the stepped portion 1333 may be larger than that of the first guide portion 1331 and that of the second guide portion 1332.

Meanwhile, the guide portion 133 may be provided with a through hole H4 through which the injection needle 11 extending from the injection needle support portion 1322 penetrates.

The through hole H4 may be formed to penetrate through the inside of the guide portion 133 (more precisely, the first guide portion 1331, the stepped portion 1333, and the second guide portion 1332).

One end of the through hole H4 may be opposed to the communication hole H3 of the injection needle support portion 1322 and the other end of the through hole H4 may be opposed to a communication hole H2 (center of a second annular wall 1314b) of the tube support portion 1314.

The pawl portion 134 may be formed to prevent a distance between the first grip portion 131 and the second grip portion 132 from becoming smaller than a predetermined value. The pawl portion 134 may be formed so that the predetermined value can be adjusted.

More specifically, the pawl portion 134 includes a ring 1341 movably coupled to the second guide portion 1332, a second pin 1342 movably coupled to the ring 1341 and a second elastic body 1343 having one side supported on the second pin 1342 and the other side supported on the ring 1341.

The ring 1341 may be formed in an annular shape and the second guide portion 1332 may penetrate through an inner circumferential part of the ring 1341. Here, the second guide portion 1332 may be inserted into the second handle 1321 after passing through the ring 1341. That is, the ring 1341 may be interposed between the stepped portion 1333 of the guide portion 133 and the second handle 1321.

A side wall of the ring 1341 may be provided with a second pinhole 1341*a* through which the second pin 1342 penetrates.

The second pinhole 1341*a* may be formed to penetrate in a radial direction of the ring 1341.

The second pin 1342 may include a second head portion 1342*a* that has a larger diameter than the second pinhole 1341*a* and a second protrusion 1342*b* that protrudes from the second head portion 1342*a*.

The second pin 1342 may be movably coupled to the first ring 1341 in the radial direction of the ring 1341 by inserting the second protrusion 1342*b* into the second pinhole 1341*a*.

The second pin 1342 may move toward a center of the ring 1341 so that the second protrusion 1342*b* is inserted into any one of the plurality of second fixing grooves 1332*a*, thereby fixing the ring 1341 to the guide portion 133.

The second pin 1342 may move toward a radial outside of the ring 1341 so that the second protrusion 1342*b* is drawn out from the second fixing groove 1332*a*, into which the second protrusion 1342*b* is inserted, among the plurality of second fixing grooves 1332*a*, thereby releasing the fixing of the ring 1341 to the guide portion 133.

The second elastic body 1343 may be a spring that applies an elastic force to the second pin 1342 in a direction in which the second protrusion 1342*b* of the second pin 1342 is inserted into the second fixing groove 1332*a*.

Here, the ring 1341 may be movable along the extension direction of the second guide portion 1332, but may be fixed at any position on the second guide portion 1332 by the second pin 1342, the second elastic body 1343, and the second fixing groove 1332*a*. The fixed position of the ring 1341 may be determined depending on which of the plurality of second fixing grooves 1332*a* of the second pin 1342 is inserted into. The fixed ring 1341 may pawl the second handle 1321 so that when the second handle 1321 approaches the first handle 1311, the second handle 1321 may not more approach the first handle 1311 after passing through the fixed position of the ring 1341.

The aspiration device 2 may include a suction cable (not shown) that is coupled to the injection needle support portion 1322 and communicates with the injection needle 11, a sound pressure generation device (not shown) that generates a sound pressure on the suction cable, and a storage container (not shown) that stores tissues sucked into the sound pressure generation device (not shown) and the suction cable (not shown). The aspiration device 2 may be formed as, for example, a piston type syringe.

The injection device 3 may include an injection cable (not shown) that is coupled to the injection needle support portion 1322 and communicates with the injection needle 11 and an injector (not shown) that injects a drug into the injection cable (not shown). The injection device 3 may be formed as, for example, a piston type syringe.

The electrode device 4 may include a power cable 41 that is coupled to the injection needle support portion 1322 and a control device (not shown) that applies power (current) to the power cable 41.

The electrode device 4 further includes a temperature sensor 42 that is inserted into the hollow of the injection needle 11 and a sensing cable 43 that connects between the temperature sensor 42 and the control device (not shown), in which the control device (not shown) controls power applied to the power cable 41 according to the temperature measured by the temperature sensor 42 so that the temperature of the injection needle 11 is maintained within a predetermined range.

The sensing cable 43 protrudes from an end of the power cable 41 by penetrating through an inside of the power cable 41 and the temperature sensor 42 may be provided at an end of the sensing cable 43. The temperature sensor 42 and the sensing cable 43 may be inserted into the hollow of the injection needle 11 by penetrating through the communication hole H3 of the injection needle support portion 1322. At this time, in connection with the temperature of the injection needle 11, a temperature of a site where the thermal treatment is performed is more important than a temperature of other sites, and therefore it may be preferable that the temperature sensor 42 is positioned at the needlepoint T where the thermal treatment is made.

When the temperature measured by the temperature sensor 42 is lower than a predetermined value, the control device (not shown) may apply power to the power cable 41, and when the temperature measured by the temperature sensor 42 is equal to or larger than the predetermined value, the control device may not apply power to the power cable 41.

Here, the electrode device 4 may be formed as an RF electrode device 4.

Hereinafter, an action and an effect of the surgical device according to the embodiment of the present invention will be described.

That is, the surgical device according to the present embodiment may be injected into a surgical site under the induction of endoscopic ultrasound (EUS) to perform the tissue sampling, the drug injection, and the thermal treatment.

More specifically, the needle device 1 may be provided in a state in which the first grip portion 131 and the second grip portion 132 are spaced apart from each other and thus the injection needle 11 is inserted into the tube 12.

The tube 12 into which the injection needle 11 is inserted passes through the inside of the endoscopic ultrasound (EUS) so that the end of the tube 12 may be opposed to the surgical site.

The protruding length of the injection needle 11 with respect to the tube 12 may be determined in consideration of a distance between the end of the tube 12 and the surgical site. The protruding length of the injection needle 11 may be determined by adjusting the position of the first grip portion 131 and the position of the pawl portion 134 with respect to the guide portion 133. The adjustment of the protruding length of the injection needle 11 will be described later. Here, the protruding length of the injection needle 11 may be adjusted before the tube 12 is inserted into the endoscopic ultrasound (EUS).

The second grip portion 132 may move toward the first grip portion 131 until the second grip portion 132 is pawled by the pawl portion 134. Therefore, the needlepoint T of the injection needle 11 protrudes from the end of the tube 12 and may be injected into the surgical site.

Any one of the aspiration device 2, the injection device 3, and the electrode device 4 may be connected to the injection needle support portion 1322.

When the aspiration device 2 is connected to the injection needle support portion 1322, the tissue sampling may be performed. That is, when the sound pressure generation device (not shown) of the aspiration device 2 is operated, the tissue is sucked from the surgical site through the injection hole H1, the hollow of the injection needle 11, the communication hole H3 of the injection needle support portion 1322, and the suction cable (not shown), and the sucked tissue may be stored in the storage container (not shown).

When the injection device 3 is connected to the injection needle support portion 1322, the drug injection may be performed. That is, if the injector (not shown) is operated, a drug may be injected into the surgical site from the injector (not shown) through the injection cable (not shown), the communication hole H3 of the injection needle support portion 1322, the hollow of the injection needle 11 and the injection hole H1.

When the electrode device 4 is connected to the injection needle support portion 1322, the thermal treatment may be performed. That is, the control device (not shown) supplies power (current) to the power cable 41 and the power (current) input to the power cable 41 may be output to the first site 111 of the injection needle 11 through the injection needle support portion 1322. The current output to the first site 111 of the injection needle 11 may apply heat (electricity) to the surgical site through the needlepoint T in the first site 111 of the injection needle 11. At this time, the second site 112 of the injection needle 11 may prevent a site other than the needlepoint T in the first site 111 of the injection needle 11 from being damaged to a site other than the surgical site. On the other hand, the temperature sensor 42 may continuously measure the temperature of the needlepoint T and the temperature information measured by the temperature sensor 42 may be transmitted to the control device (not shown) through the sensing cable 43. The control device (not shown) controls power (current) applied to the power cable 41 based on the temperature information to maintain the temperature of the injection needle 11 (more precisely, the needlepoint T) in a predetermined range. Thus, more accurate thermal treatment may be made. That is, since the temperature of the needlepoint T is lower than a lower limit of the predetermined range, the thermal treatment is not made or since the temperature of the needlepoint T is higher than an upper limit of the predetermined range, it is possible to prevent the surgical site from being damaged.

When all of the tissue sampling, the drug injection, and the thermal treatment are performed, the aspiration device 2, the injection device 3, and the electrode device 4 may be sequentially and alternately attached to or detached from the injection needle grip portion 1322. The attachment or detachment sequence may be adjusted appropriately.

When one or two of the tissue sampling, the drug injection, and the thermal treatment are performed, the device corresponding to the treatment to be performed among the aspiration device 2, the injection device 3, and the electrode device 4 may be attached to or detached from the injection needle grip portion 1322. When the two treatments are performed, the devices used for each treatment may be sequentially attached to or detached from the injection needle support portion 1322 and the attachment or detachment sequence may be adjusted appropriately.

In the case of the present embodiment, the devices (aspiration device 2 or injection device 3 or electrode device 4) used for the initial treatment during the tissue sampling, the drug injection, and the thermal treatment are mounted on the injection needle support portion 1322 in the state in which the needlepoint T is injected into the surgical site or may be mounted on the injection needle support portion 13222 before the needlepoint T is injected into the surgical site.

After all the treatments are completed, the first grip portion 131 and the grip portion 132 may be spaced apart from each other to insert the injection needle 11 into the tube 12 and detach the needle device 1 from the endoscopic ultrasound (EUS).

Here, in the surgical device according to the present invention, any one of the aspiration device 2, the injection device 3 and the electrode device 4 is attached to or detached from and attached to the needle device 1 such that the needle device 1 may perform at least one of the tissue sampling, the drug injection, and the thermal treatment in the state in which the needle device 1 is injected into the surgical site. Therefore, it is possible to reduce the time and costs required for the tissue sampling, the drug injection, and the thermal treatment. That is, it is not necessary to provide separate dedicated surgical devices for each treatment, such that the time and costs required for each dedicated surgical device may be reduced. The time and costs required to replace each dedicated surgical device may be reduced. When the surgical device is replaced, it is possible to prevent each of the dedicated surgical devices from being injected into different surgical sites. In addition, it is possible to prevent foreign matters from being introduced into the surgical site during the process of replacing the surgical device.

On the other hand, the protruding length of the injection needle 11 may be adjusted depending on the positions of the pawl portion 134 and the first grip portion 131 with respect to the guide portion 133.

More specifically, the injection needle 11 may be coupled to the first handle 1311 and may move together with the first handle 1311. In other words, the injection needle 11 may move forward until the first handle 1311 touches the pawl portion 134. At this time, the protruding length of the injection needle 11 is proportional to the distance between the pawl portion 134, and the tube 12 and the distance between the pawl portion 134 and the tube 12 may be proportional to a sum of the distance between the stepped portion 1333 of the guide portion 133 and the pawl portion 134 and a distance between the stepped portion 1333 and the first handle 1311.

The distance between the stepped portion 1333 and the pawl portion 134 may be determined depending on which of the plurality of second fixing grooves 1332a of the second pin 1342 is inserted into. That is, the distance may be determined depending on the position of the pawl portion 134 with respect to the guide portion 133. Referring to FIG. 11 the pawl portion 134 moves in a direction in which the second pin 1342 is away from the second guide portion 1332, such that the second protrusion 1342b may be drawn out from the second fixing groove 1332a. In this state, the pawl portion 134 may move along the second guide portion 1332. The pawl portion 134 moving to the desired position moves in a direction in which the second pin 1342 approaches the second guide portion 1332, such that the second protrusion 1342b may be inserted into one of the plurality of second fixing grooves 1332a to be fixed to the second guide portion 1332. At this time, the second elastic body 1343 applies an elastic force in a direction in which the second pin 1342 is inserted into the second fixing groove 1332a, and therefore when the pawl portion 134 moves, an operator needs to apply a force to the second pin 1342 in a direction in which the second pin 1342 is drawn out from the second fixing groove 1332a but when the second pawl portion 134 is fixed, if an operator puts the second pin 1342, the second pin 1342 may move by an elastic restoring force of the second elastic body 1343 to be inserted into the second fixing groove 1332a.

The distance between the stepped portion 1333 and the first handle 1311 may be determined depending on which of the plurality of first fixing grooves 1331*a* the first pin 1312 is inserted into. That is, the distance may be determined depending on the position of the first handle 1311 with respect to the guide portion 133. The position of the first handle 1311 may be determined on the same principle as the pawl portion 134. Although not shown separately, the first handle 1311 moves in a direction in which the first pin 1312 is away from the first guide portion 1331 such that the first protrusion 1312*b* may be drawn out from the first fixing groove 1331*a*. In this state, the first handle 1311 may move along the first guide portion 1331. The first handle 1311 moving to the desired position moves in a direction in which the first pin 1312 approaches the first guide portion 1331, such that the first protrusion 1312*b* may be inserted into one of the plurality of first fixing grooves 1331*a* to be fixed to the first guide portion 1331. At this time, the first elastic body 1313 applies an elastic force in a direction in which the first pin 1312 is inserted into the first fixing groove 1331*a*, and therefore when the first handle 1311 moves, an operator needs to apply a force to the first pin 1312 in a direction in which the first pin 1312 is drawn out from the first fixing groove 1331*a*, but when the first handle 1311 is fixed, only if an operator puts the first pin 1312, the first pin 1312 may move by an elastic restoring force of the first elastic body 1313 to be inserted into the first fixing groove 1331*a*.

Here, in the case of the present embodiment, the distance between the plurality of first fixing grooves 1331*a* is smaller than the distance between the plurality of second fixing grooves 1332*a*, such that the position (the distance between the stepped portion 1333 and the pawl portion 134) of the pawl portion 134 may be adjusted to a relatively larger scale and the position (the distance between the stepped portion 1333 and the first handle 1311) of the first handle 1311 may be adjusted to a relatively smaller scale. Accordingly, a considerable amount of protruding length may be easily adjusted by the pawl portion 134, and the fine adjustment of the protruding length may be easily made by the first handle 1311.

In addition, in the case of the present embodiment, the position of the pawl portion 134 and the first handle 1311 is adjusted in such a manner that the operator pulls and releases the first pin 1312 or the second pin 1342, and therefore an operator may adjust the position of the pawl part 134 or the first handle 1311 with one hand while gripping the operating device 13 with the other hand. That is, the position of the pawl portion 134 and the first handle 1311 may be easily adjusted.

On the other hand, in the case of the present embodiment, the operation device 13 may be formed so that the protruding length of the injection needle 11 is adjusted even by the pawl portion 134 and is adjusted even by the first handle 1311, but the protruding length of the injection needle 11 is adjusted only by the pawl portion 134 or only by the first handle 1311.

Further, in the case of the present embodiment, the electrode device 4 includes the power cable 41, the temperature sensor 42, the sensing cable, and the control device (not shown), but may include only the power cable 41 and the control device (not shown).

In addition, in the case of the present embodiment, to facilitate the tissue sampling and the drug injection, the needlepoint T of the injection needle 11 (more precisely, the first site 111) is obliquely cut so that a part of the circumference thereof stands on end, in which the cut surface is provided with the injection hole H1 but other embodiments may exist.

FIG. 12 is a cross-sectional view showing another embodiment of the needlepoint in the needle device of FIG. 6, and FIG. 13 is a side view of FIG. 12.

Referring to FIGS. 12 and 13, the needlepoint T according to another embodiment of the present invention includes a cylindrical portion T1 having a hollow cylindrical shape and a vertex portion T2 protruding a front end surface of the cylindrical portion T1. The vertex portion T2 may have a polygonal pyramid or cone shape so that the injection needle 11 may easily penetrate through a tissue while contacting (concentration of a pressure on one point) the tissue in a point-contact manner.

Here, the vertex portion T2 may have a triangular pyramid shape to be easily processed while maintaining a penetration force at an equal level, but may have a quadrangular pyramid shape. In this case, the manufacturing cost may be increased because the processing is somewhat more difficult than in the above-described embodiment, but the manufacturing costs may be increased but the penetration force may be improved. In addition, the vertex portion T2 may have a cone shape. In this case, the manufacturing cost is increased because of the difficulty in processing as compared with the above-described embodiment, but when the injection needle 11 rotates and moves forward because there is no angled portion on an inclined surface of the vertex portion T2, the injection needle 11 may easily rotate, the tissue damage may be minimized, and penetration force may be further improved. Here, the injection needle 11 may rotate by allowing an operator to rotate the operating device 13, and a rotating device for rotating the injection needle 11 may be provided inside the operating device 13, and thus the injection needle 11 may also rotate by the rotating device.

The vertex portion T2 prevents the injection needle 11 from being injected into a position different from a predetermined position due to the bending of the injection needle 11 when the injection needle 11 is injected into a surgical site, and a vertex V of the vertex portion T2 may be positioned on a central axis of the injection needle 11 to further improve the penetration force of the injection needle 11.

More specifically, when the vertex V is not positioned on the central axis of the injection needle 11, the injection needle 11 may be bent by a lateral force applied in a direction different from a movement direction (direction in the central axis of the injection needle 11) of the injection needle 11 when the injection needle 11 is injected into the surgical site. As a result, there may be the problem in that the penetration force of the injection needle 11 is reduced and the injection of the injection needle 11 is not easy, and the injection needle 11 may be injected into a position different from the predetermined position. In consideration of this, the vertex V is formed so as to be positioned on the central axis of the injection needle 11, thereby preventing the lateral force from occurring. Therefore, the injection needle 11 may be prevented from being bent when being injected into the surgical site, the penetration force of the injection needle 11 may be further improved, the injection needle 11 may be easily injected, and the injection needle 11 may be injected into the predetermined position.

In addition, the injection needle 11 may rotate and move forward to easily penetrate through a tissue. In this case, if the vertex V is positioned on the central axis of the injection needle 11, the vertex V rotates with respect to one point, such that the penetration force may be improved and the tissue damage may be minimized.

A conical angle (angle between main lines of the vertex portion T2 with respect to the vertex V) may be in a range of an acute angle so that the vertex portion T2 increases sharpness of the vertex V to further improve the penetration force of the injection needle 11. That is, the vertex portion T2 may be formed so that a distance (height of a cone) from a front end surface of the cylindrical portion T1 to the vertex V is longer than a distance (radius of a bottom of a horn) from the central axis of the injection needle 11 to an outer circumferential surface of the cylindrical portion T1.

On the other hand, the injection hole H1 may be formed at the vertex portion T2 but may be formed on the sidewall of the cylindrical portion T1 in the radial direction of the cylindrical portion T1 so as not to reduce the penetration force of the injection needle 11.

The injection hole H1 may be formed in plural to more facilitate the tissue sampling and the drug injection.

The plurality of injection holes H1 may be arranged at equal intervals along the circumferential direction of the first site 111 so that the tissue sampling and the drug injection may be performed at the same position.

INDUSTRIAL APPLICABILITY

The present invention relates to a surgical device, and more particularly, to a surgical device capable of performing medical treatment through a needle.

According to the surgical device of the present invention any one of the aspiration device, the injection device, and the electrode device is attached to or detached from the needle device, thereby being capable of performing the tissue sampling, the drug injection, and the thermal treatment. Thus, the time and costs required for the tissue sampling, the drug injection, and the thermal treatment can be reduced and foreign substances can be prevented from flowing into the surgical site in advance.

The invention claimed is:

1. A surgical apparatus, comprising: a needle device having an injection needle, and a sheath surrounding the injection needle; and
   an electrode device detachably attached to the needle device for thermal treatment,
   an operating device configured to move the injection needle so that a needlepoint of the injection needle protrudes from the sheath or is contained within the sheath,
   wherein the injection needle includes a first tube having a hollow shape and having an injection hole disposed in a distal end of a needlepoint portion, and a second tube partially surrounding the first tube along a length of the injection needle, the first tube being made of a conductive material and the second tube being made of an insulating material,
   wherein the needlepoint portion of the first tube is not surrounded by the second tube,
   wherein the electrode device includes a temperature sensor disposed in a hollow space within the first tube of the injection needle, and
   wherein the temperature sensor is located at a position in the hollow space within the first tube in the needlepoint portion and configured to measure a temperature of the needlepoint portion at the position in the hollow space,
   wherein the operating device includes:
   a guide tube in which at least a portion of the needle device is movably accommodated, and having a plurality of fixing grooves along a length thereof;
   a front grip handle directly coupled to the sheath and movable with respect to the guide tube;
   a rear grip handle movable with respect to the guide tube, wherein the rear grip handle is coupled to the injection needle and configured to approach and retreat from the front grip handle along the guide tube so as to reciprocally move the injection needle with respect to the sheath; and
   a stopper movably disposed at an intermediate portion of the guide tube between the front grip handle and the rear grip handle, wherein the stopper is configured to restrict a movement of the rear grip handle along the guide tube to prevent a distance between the front grip handle and the rear grip handle from being smaller than a predetermined value,
   wherein the stopper includes;
   a ring having an annular shape through which the guide tube movably penetrates, the ring having a pinhole disposed in a radial direction thereof;
   a pin movably coupled to the ring in the radial direction, wherein the pin has a head portion that has a larger diameter than the pinhole and a protrusion that protrudes from the head portion, wherein the protrusion of the pin is disposed in the pinhole to be moved toward a center of the ring or toward a radial outside of the ring so as to be engaged with or released from one of the plurality of fixing groves; and
   an elastic body disposed in the pinhole and configured to apply an elastic force to the pin in an engaging direction thereof.

2. The surgical apparatus of claim 1, wherein the electrode device includes a radio frequency (RF) electrode.

3. The surgical apparatus at claim 1, wherein the electrode device includes: a power cable electrically connected to the injection needle; and a control device configured to apply power to the power cable.

4. The surgical apparatus of claim 3, wherein the electrode device further includes:
   a sensing cable disposed to connect the temperature sensor to the control device.

5. The surgical apparatus of claim 4, wherein the control device controls power applied to the power cable depending on the temperature measured by the temperature sensor so that the temperature of the needlepoint portion of the injection needle is maintained to be in a predetermined range.

6. The surgical apparatus of claim 5, wherein the control device applies power to the power cable when the temperature measured by the temperature sensor is smaller than a predetermined value, and does not apply power to the power cable when the temperature measured by the temperature sensor is equal to or larger than the predetermined value of the temperature.

7. The surgical apparatus of claim 1, wherein the needlepoint portion includes:
   a cylindrical portion having a hollow cylindrical shape; and
   a vertex portion having a polygonal pyramid or cone shape protruding from a front end of the cylindrical portion.

8. The surgical apparatus of claim 7, wherein a vertex of the vertex portion is positioned on a central axis of the injection needle.

9. The surgical apparatus of claim 7, wherein an injection hole is formed at the cylindrical portion.

10. The surgical apparatus of claim 9, wherein the injection hole is formed to penetrate the cylindrical portion in a radial direction.

11. The surgical apparatus of claim 9, wherein the injection hole includes a plurality of holes, and the plurality of holes are arranged at equal intervals along a circumferential direction of the cylindrical portion.

\* \* \* \* \*